(12) United States Patent
Benda et al.

(10) Patent No.: US 9,393,176 B2
(45) Date of Patent: Jul. 19, 2016

(54) INFRARED HEATING PANELS WITH NON-LINEAR HEAT DISTRIBUTION

(71) Applicant: TyloHelo Inc., Cokato, MN (US)

(72) Inventors: Steven J. Benda, Cokato, MN (US); Ragis H. C. Kao, Taipei (CN); Chad M. Benda, Cokato, MN (US)

(73) Assignee: TyloHelo, Inc., Cokato, MN (US)

( * ) Notice: Subject to any disclaimer, the term of this patent is extended or adjusted under 35 U.S.C. 154(b) by 68 days.

(21) Appl. No.: 14/170,967

(22) Filed: Feb. 3, 2014

(65) Prior Publication Data

US 2014/0215708 A1 Aug. 7, 2014

Related U.S. Application Data

(60) Provisional application No. 61/849,744, filed on Feb. 1, 2013.

(51) Int. Cl.
*A61H 33/06* (2006.01)
*B23K 13/08* (2006.01)
(Continued)

(52) U.S. Cl.
CPC ............ *A61H 33/063* (2013.01); *A61H 33/066* (2013.01); *A61N 5/0625* (2013.01); *H05B 3/26* (2013.01); *A61B 2018/00702* (2013.01);
(Continued)

(58) Field of Classification Search
CPC . A61H 33/066; A61H 33/063; A61N 5/0625; H05B 3/26
USPC ........ 4/524; 219/476–478; 392/435, 407, 416
See application file for complete search history.

(56) References Cited

U.S. PATENT DOCUMENTS

| 4,468,557 A | 8/1984 | Bylin et al. |
| 4,485,297 A | 11/1984 | Grise |

(Continued)

FOREIGN PATENT DOCUMENTS

| CA | 2813340 A1 | 7/2013 |
| CA | 2813340 | 7/2014 |

(Continued)

OTHER PUBLICATIONS

Translation of WIPO Publication of WO-2009065265, dated Oct. 2008, 1 page.

(Continued)

*Primary Examiner* — Huyen Le
*Assistant Examiner* — Christine Skubinna
(74) *Attorney, Agent, or Firm* — Pauly, Devries Smith & Deffner, LLC

(57) ABSTRACT

Examples of infrared heating panels are described as having a non-linear power density profile along a length of the heating panel. The power density profile can include a first power density zone and a second power density zone, each zone corresponding to an area of the heating panel having a separate power density in response to a current flow. An infrared heating panel can include multiple heating elements arranged adjacently in a row and electrically connected together by at least two power buses extending perpendicularly across the heating elements. In one example, the first power density zone is located between a first power bus and an end of the heating elements. The second power density zone can be located between the first power bus and an opposite end of the heating elements. Infrared sauna systems and methods of generating heat for a sauna are also provided.

20 Claims, 16 Drawing Sheets

(51) Int. Cl.
  *H05B 3/68* (2006.01)
  *F24D 19/02* (2006.01)
  *H05B 3/26* (2006.01)
  *A61N 5/06* (2006.01)
  *A61B 18/00* (2006.01)

(52) U.S. Cl.
  CPC ..... *A61H2201/10* (2013.01); *A61N 2005/0636* (2013.01); *A61N 2005/0659* (2013.01); *H05B 2203/011* (2013.01); *H05B 2203/032* (2013.01); *H05B 2203/037* (2013.01)

(56) References Cited

U.S. PATENT DOCUMENTS

| | | | |
|---|---|---|---|
| 4,583,815 | A | 4/1986 | Taga et al. |
| 4,959,527 | A | 9/1990 | Kivimaa |
| 4,998,006 | A | 3/1991 | Perlman |
| 5,155,800 | A | 10/1992 | Rezabek et al. |
| 5,399,996 | A | 3/1995 | Yates |
| 5,410,127 | A | 4/1995 | LaRue |
| 5,874,712 | A | 2/1999 | Toth et al. |
| 5,908,573 | A | 6/1999 | Chiles |
| 5,912,811 | A | 6/1999 | Mackta |
| 6,300,597 | B1 | 10/2001 | Lee |
| 6,734,404 | B2 | 5/2004 | Hays |
| 6,745,411 | B1 | 6/2004 | Kjonaas |
| 7,120,353 | B2 | 10/2006 | Schaeffer |
| 7,142,779 | B2 | 11/2006 | Schaeffer |
| 7,329,843 | B2 | 2/2008 | Bikhovsky |
| 8,692,168 | B2 | 4/2014 | Benda et al. |
| 2003/0156831 | A1 | 8/2003 | Schaeffer |
| 2003/0178415 | A1 | 9/2003 | Hays et al. |
| 2004/0184793 | A1 | 9/2004 | Schaeffer |
| 2007/0145041 | A1 | 6/2007 | Shim |
| 2007/0182498 | A1 | 8/2007 | Zumoto et al. |
| 2010/0266267 | A1 | 10/2010 | Chu |
| 2011/0081135 | A1 | 4/2011 | Felder |
| 2011/0315672 | A1 | 12/2011 | Benda |
| 2013/0068754 | A1* | 3/2013 | Ptasienski ............... H05B 3/26 219/541 |
| 2013/0105458 | A1 | 5/2013 | Benda et al. |
| 2013/0319998 | A1 | 12/2013 | Benda et al. |

FOREIGN PATENT DOCUMENTS

| | | |
|---|---|---|
| DE | 1615494 A1 | 2/1971 |
| DE | 3843074 A1 | 7/1989 |
| EP | 2668938 | 12/2013 |
| EP | 2531775 | 3/2015 |
| GB | 589752 A | 6/1947 |
| JP | 05343167 | 12/1993 |
| WO | 00-70270 | 11/2000 |
| WO | 2008105612 | 9/2008 |
| WO | 2009065265 | 5/2009 |
| WO | 2009065265 A1 | 5/2009 |
| WO | 2011097086 | 8/2011 |

OTHER PUBLICATIONS

Notice of Allowance for U.S. Appl. No. 12/966,221, dated Nov. 25, 2013, 14 pages.
"EMF Documentation," Welcome to the Wellness Center, http://www.wellnesscener.net/resources,articles/EMF/EMF_Doc.htm,printed Dec. 30, 2009, 3 pages.
English translation of claims of DE1615494 (German claims published Feb. 25, 19791; translated Nov. 18, 2011) 2 pages.
International Search Report for PCT/US2011/022215, dated Nov. 11, 2011, 13 pages.
Canadian Office Action for Application No. 2,729,500, dated Oct. 17, 2011, 3 pages.
Communication Pursuant to Article 94(3) EPC for European Patent Application No. 13169699.9, mailed Oct. 29, 2014 (5 pages).
Communication Under Rule 71(3) EPC for European Patent Application No. 13169699.9, mailed Nov. 13, 2015 (25 pages).
Non-Final Office Action for U.S. Appl. No. 13/837,087 mailed Sep. 15, 2015 (17 pages).
Response to Examiner's Requisition for Canadian Patent Application No. 2,841,497, mailed Sep. 26, 2014 and filed with the Canadian Patent Office Dec. 23, 2014 (5 pages).

* cited by examiner

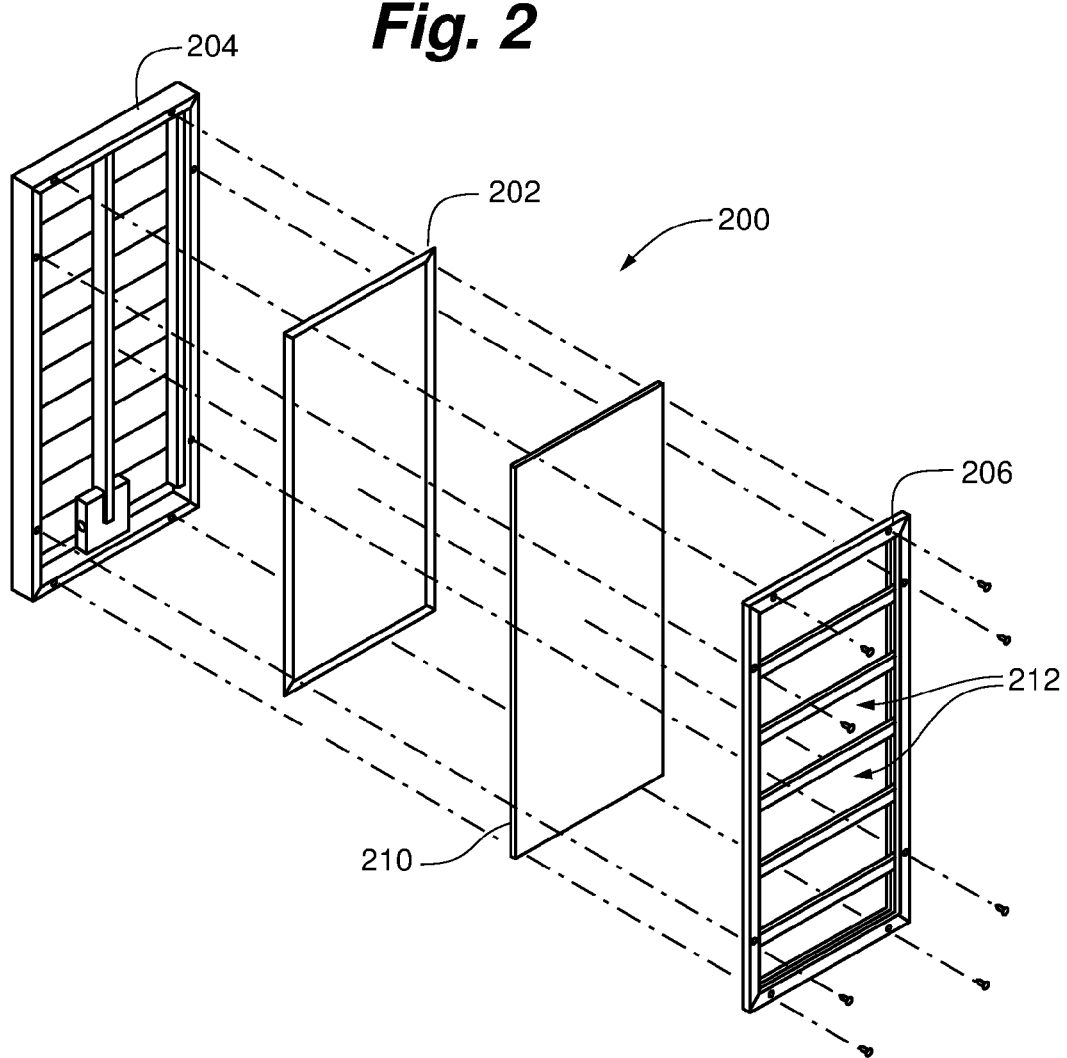

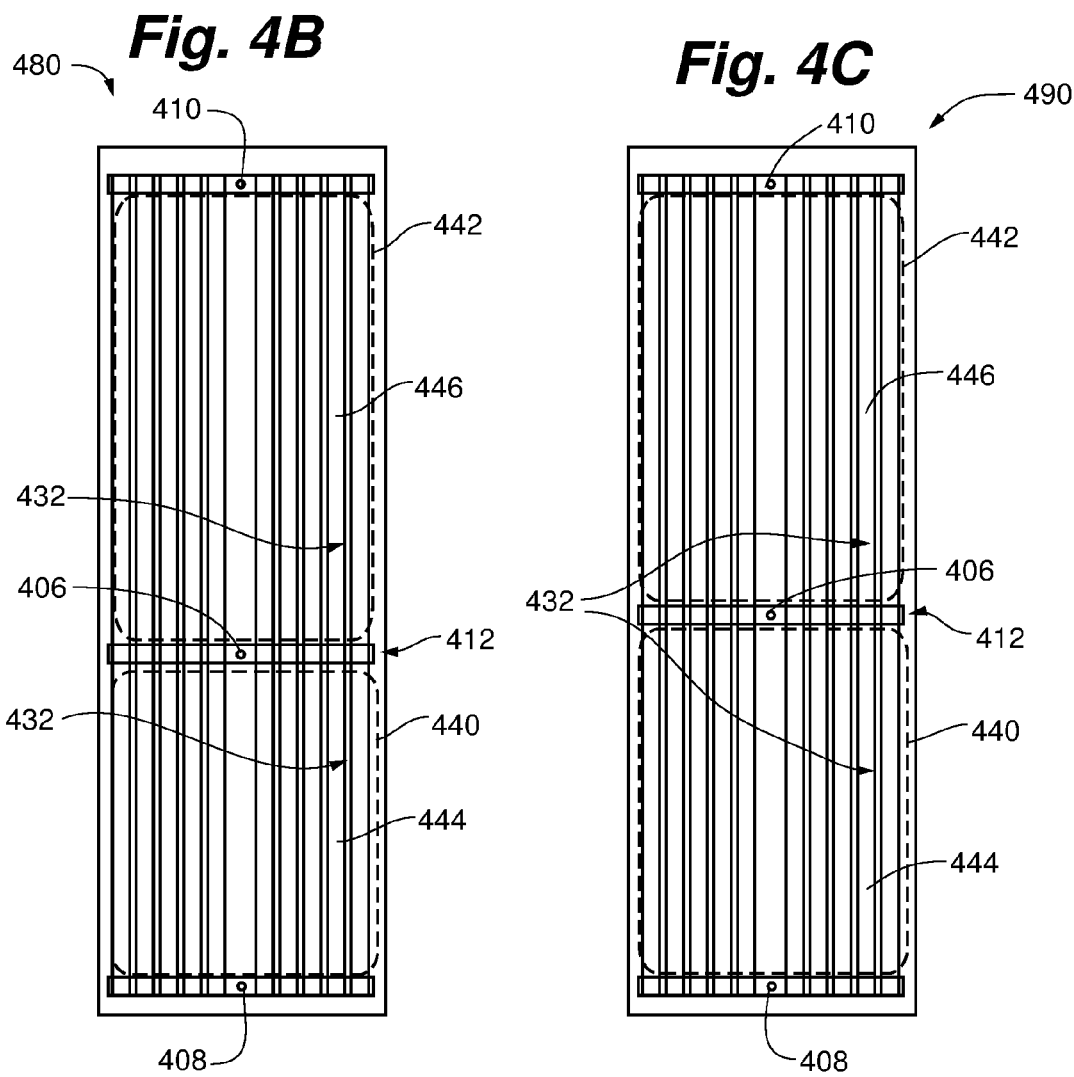

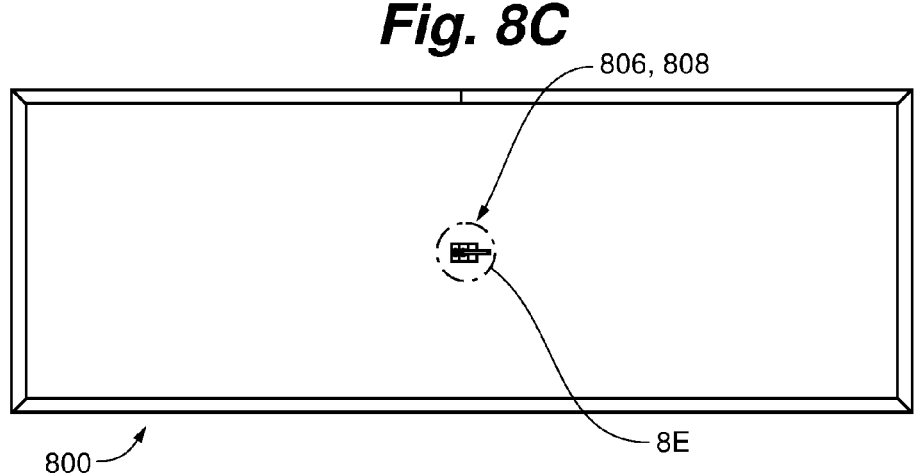
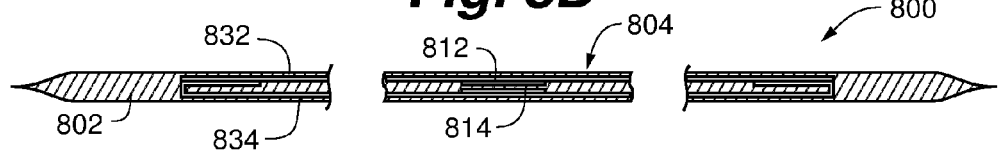
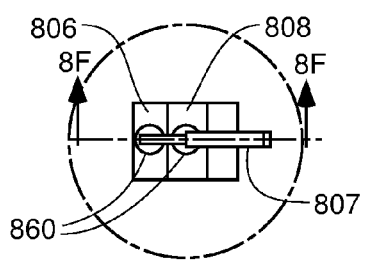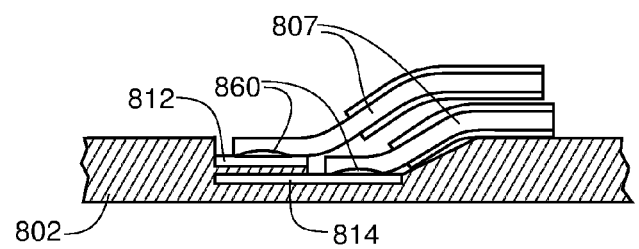

INFRARED HEATING PANELS WITH NON-LINEAR HEAT DISTRIBUTION

CROSS-REFERENCES

This application claims the benefit of U.S. Provisional Application No. 61/849,744 filed Feb. 1, 2013, the content of which is hereby incorporated by reference in its entirety.

FIELD

This disclosure relates generally to infrared saunas, and relates more particularly to infrared heating panels, systems and methods used for infrared saunas.

BACKGROUND

Sauna systems throughout history have employed various methods of heating a space to provide the therapeutic and cleansing effects of heat. As is well known, heat causes the human body to perspire and can also provide soothing and therapeutic effects to muscles and joints. Known systems for heating a sauna have included using open fires, enclosed stoves, and steam generators among others. While these systems have had varying degrees of effectiveness, each has further been found to present drawbacks. For example, systems using open fires, while providing direct open-flame heating, have been found to result in smoke-filled sauna rooms. Additionally, the heat created from such open fires is often short lived. On the other hand, wood stoves have been found to enable a more controlled heat over a greater period of time, but also shield the heat due to the enclosed nature of the stoves.

Electrically energized heaters, including electrically-resistive heaters and energized radiant heaters, have also been developed and have gained popularity for their use in saunas. Some radiant heat systems are known to employ infrared heating panels to generate electromagnetic radiation within the infrared spectrum. When absorbed by the body of a sauna user, the infrared radiation excites the molecules within the body to generate warming. Whereas steam or warm air generally only heat the skin and tissue directly beneath by conduction, infrared radiation more deeply penetrates the body (e.g., to about 1.5 inches) to more effectively and comfortably warm the body to a sweating temperature without the use of a conductive medium.

SUMMARY

Embodiments of the invention described herein generally relate to infrared heating panels and generating infrared radiation for use in a sauna. According to some embodiments, an infrared heating panel has a first power density zone and a second power density zone. The panel further includes an electrically insulative planar substrate and a plurality of infrared heating elements carried by the substrate. In certain cases, each heating element has a first end, a second end, and an elongated segment extending between the first end and the second end. The heating panel also includes a first power bus and a second power bus. Each bus extends perpendicularly across and electrically connects with each of the plurality of heating elements.

As will be discussed, in certain cases the first power bus is electrically connected to the elongated segments between the first end and the second end of each of the heating elements. The elongated segment of each heating element includes an electrically resistive material adapted to emit infrared radiation in response to a current flow. A first segment portion extends into the first power density zone between the first power bus and the first end of the heating element and is configured to generate a first power density in response to a current flow. A second segment portion extends into the second power density zone between the first power bus and the second end of the heating element. The second segment portion is configured to generate a second power density in response to a current flow. The second power density is separate from the first power density.

According to another aspect of some embodiments, an infrared sauna is provided with an enclosed room and at least one infrared heating panel. The room provides a floor, a ceiling, and a plurality of walls extending between the floor and the ceiling. The infrared heating panel has a top edge and a bottom edge and is mounted to one of the walls in a vertical orientation with the bottom edge nearest the floor and the top edge nearest the ceiling. The infrared heating panel includes an electrically insulative planar substrate and a plurality of infrared heating elements carried by the substrate. Each heating element comprises a bottom end proximate the bottom edge of the heating panel, a top end proximate the top edge of the heating panel, and an elongated segment extending between the bottom end and the top end.

The heating panel further includes at least a first power bus and a second power bus. Each power bus extends perpendicularly across and electrically connects with each of the plurality of heating elements. More specifically, the first power bus is electrically connected to the elongated segments between the bottom end and the top end of each of the heating elements, which thus defines a first power density zone located between the first power bus and the bottom ends of the heating elements and a second power density zone located above the first power density zone between the first power bus and the top ends of the heating elements. According to some embodiments, the first power density zone generates a first power density in response to currents flowing through the heating elements between the first power bus and the bottom ends of the heating elements. The second power density zone generates a second power density in response to currents flowing through the heating elements between the first power bus and the top ends of the heating elements.

Another aspect of certain embodiments includes a method for heating an infrared sauna. The method includes applying power to one or more infrared heating panels. Each infrared heating panel has a top edge and a bottom edge, and the heating panel is mounted to a wall of the sauna in a vertical orientation with the bottom edge nearest a floor of the sauna and the top edge nearest a ceiling of the sauna. Each infrared heating panel includes an electrically insulative planar substrate, a plurality of infrared heating elements, a first power bus, and a second power bus. Each heating element has an elongated segment extending between a bottom end of the heating element proximate the bottom edge of the heating panel and a top end of the heating element proximate the top edge of the heating panel.

The method further includes introducing first and second currents from the first power bus into respective first and second portions of the elongated segment of each of the heating elements. The first current is flowed through the first portion of the elongated segment between the first power bus and the bottom end of the heating element to generate infrared radiation at a first power density for heating a human in the infrared sauna. The second current is flowed through the second portion of the elongated segment between the first power bus and the top end of the heating element to generate infrared radiation at a second power density different than the first power density.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 2 is an exploded assembly view of an infrared heating panel assembly according to an embodiment of the invention.

FIGS. 4A-4C are surface views of infrared heating panels depicting configurations of heating elements according to various embodiments of the invention.

FIG. 8C is a surface view of the infrared heating panel of FIG. 8A.

FIG. 8D is a cross-sectional view of the heating panel of FIG. 8C a connection location of the heating panel.

FIG. 8E is an enlarged view of a portion of the heating panel in FIG. 8C.

FIG. 8F is a cross-sectional view of the portion of the heating panel shown in FIG. 8E.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
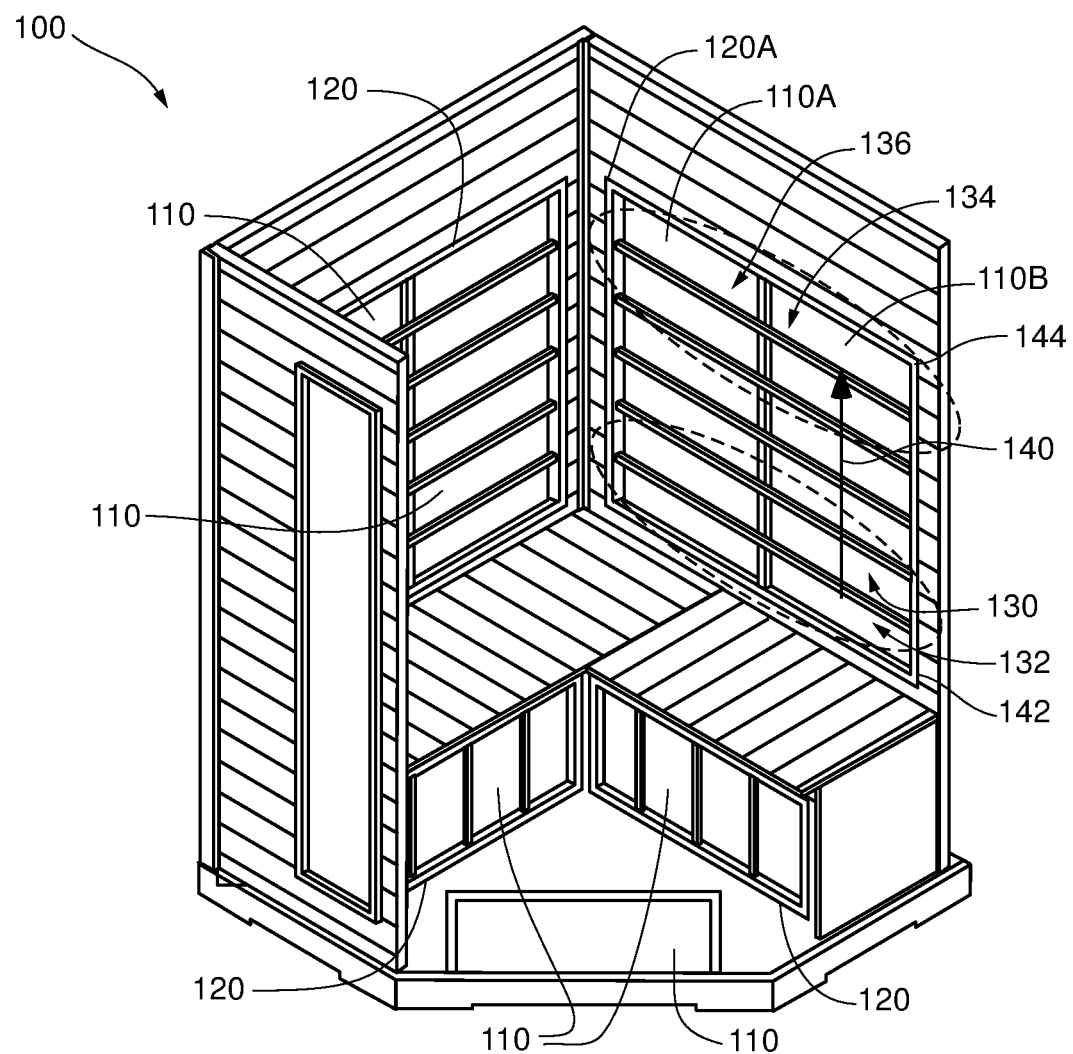
FIG. 1 is a perspective view of an infrared sauna according to an embodiment of the invention.

FIG. 1 is a perspective view of an infrared sauna 100 according to an embodiment of the invention. The sauna 100 includes a number of infrared heating panel assemblies 120 that incorporate one or more infrared heating panels 110. The heating panel assemblies 120 are positioned (e.g., mounted) on the walls, floor, and bench of the sauna 100 to surround a sauna user with IR heat. When powered, the infrared heating panels 110 generate infrared radiation for warming a person within the sauna 100.

It should be appreciated that the sauna 100 depicted in FIG. 1 is just one of many possible designs and that embodiments of the invention may include a wide variety of sauna designs. In addition, the infrared heating panels 110 may be provided with a number of physical dimensions and configurations to accommodate the overall sauna design and provide a desired heating environment. Embodiments of the invention are not limited in this regard. As just one example, the sauna 100 shown in FIG. 1 includes a number of differently sized heating panel assemblies 120 for positioning in different locations of the sauna. Further, each heating panel assembly 120 may enclose just one infrared heating panel 110, or may enclose two or more panels of the same or different size.

As will be discussed further herein, in some embodiments the heating panels 110 are configured with a particular power density profile that generates and distributes IR heat according to a desired heat profile. One example is an infrared heating panel with a power density profile that provides a heat profile with at least two different heat zones. In some cases a power density profile and corresponding heat profile can include discrete transitions between zones of different power density and between different heat zones. As used in this description, the term 'non-linear' is used to describe a panel that generates discrete changes in power, heat, and/or temperature along a dimension of the heating panel. Discrete, or non-linear, changes in these properties give rise to 'non-linear' profiles of power density, heat, and/or temperature with respect to that dimension of the panel. As a shorthand reference, heating panels configured with this type of profile are referred to herein as 'non-linear' heating panels.

Referring back to FIG. 1, in this embodiment an infrared heating panel assembly 120A is mounted to a vertical wall of the sauna 100. The assembly 120A includes a first infrared heating panel 110A and a second infrared heating panel 110B. The heating panels 110A, 110B generate radiant heat according to a heat profile that generally characterizes the amount of heat generated by zones on the heating panels that have separate power densities according to a specified power density (watts/unit square area) profile. In some embodiments the separate power density zones can exhibit different power densities, though this is not required in all embodiments.

In this case the power density profile of the heating panels 110A, 110B includes at least a first power density zone 130, which is located near a bottom edge 142 of the panels 110A, 110B as they are vertically mounted in the sauna 110. The first power density zone 130 corresponds to a first heat zone 132 that forms part of the panels' overall heat profile. A second zone 134 having a different power density than the first zone 130 is located near a top edge 144 of the panels and corresponds to a second heat zone 136. The first and second heat zones 132, 136 provide different amounts of radiant heat corresponding to the different power densities of the zones 130, 134, respectively, and thus form part of the heat profile for the heating panels.

In addition to generating radiant heat, the powered heating panels 110 also tend to generate an amount of heat that is conducted through the panel material to its surroundings, and also an amount of heat in the space surrounding the heating panel 110 by convection. As is known, warm air will rise compared to colder air. Thus, the heating panels 110A, 110B may generate a convection current 140 that tends to carry heat away from the bottom of the heating panel assembly 120A toward the top of the heating panel assembly 120A.

While other types of new and old sauna heating panels generate this type of convection current, the extra heat that collects at the top of known heating panels can lead to undesirably high panel temperatures, especially near the top of the panel, and also colder temperatures near the bottom of a panel next to where a user may be sitting. In the past one approach to mitigate this 'chimney effect' was to decrease the power being applied to a heating panel. Decreasing the applied power, however, also directly leads to a lower radiant heat output that may affect the comfort of a sauna user and/or the total heat output for a panel of a given size.

Some embodiments of Applicant's heating panels address, and may in some cases reduce, the chimney effect associated with older heating panel styles. As mentioned above, some embodiments provide an infrared heating panel that has a heat profile including two or more heat zones of different temperature. With respect to FIG. 1, for example, the heating panels 110A, 110B each have two separate zones of power density 130, 134. Each zone 130, 134 is configured so that its power density is separate from the power density of the other zone. These different zones 130, 134 of power density give rise to separate heat zones 132, 136 respectively, forming a heat profile for the panels.

According to some embodiments, the transition between the different zones 130, 134 of power density on the panels 110A, 110B is not gradual and/or is non-linear. For example, in some cases each panel's power density profile may include one, two, or more discrete steps up or down in power density between the different power density zones 130, 134. In certain embodiments, some portions of a heating panel may not generate any power, and thus the power density profile may be discontinuous.

Turning back to FIG. 1, in this particular example the heating panels of the assembly 120A are configured to provide two separate zones of power density, one zone 130 being located near the bottom edge 142 of the panel assembly and the other zone 134 being located near the top edge 144 of the panel assembly 120A. Although not illustrated, the power density profile of the heating panels includes a discrete change in power density that separates the two separate zones 130, 134. In some cases the discrete power density change corresponds to a physical aspect of the heating panels 110A, 110B that physically marks the change in the power density profile and/or otherwise physically separates the two zones 130, 134. In certain cases the change may also or instead correspond to the location of an electrical component of the heating panel. In these cases, the component may provide an electrical discontinuity on the heating panel between the two separate power density zones 130,134. Further, in some cases such an electrical component of the heating panel may also determine, at least in part, the generated power density of each power density zone. According to some embodiments, the electrical component may cause, at least in part, each power density zone to have a different power density than the other.

One example of an electrical component useful in certain embodiments is at least one common bus bar, power bus, and/or grounding bus positioned on the heating panel. The bus provides a point of electrical discontinuity between two or more circuits connected to the bus. As will be discussed further herein, in this example a power bus marks the discontinuous transition from one power density zone 130 to the other power density zone 134. In some cases the relative placement of the bus on the heating panel in part determines the physical dimensions and locations of the two power density zones 130, 134, as well as the size and placement of the corresponding different heat zones 132, 136.

FIG. 2 is an exploded assembly view of an infrared heating panel assembly 200 according to some embodiments. The panel assembly 200 generally provides an enclosure for a heating panel 202, such as one or more of the heating panels described herein. In certain embodiments the panel assembly includes a back frame member 204 and a front frame member 206 that enclose the heating panel 202 and are coupled with fastening members such as screws. Although not shown in this depiction, the heating panel 202 includes an electrical connection, such as power conductors, for connecting the infrared heating panel 202 to a source of alternating current. The panel assembly 200 also includes a thermal shielding layer 210 that can be useful for shielding a sauna user from incidental or temporary contact with the heating elements. For example, the thermal shielding layer 210 may be a cloth panel that provides a mild thermal conductivity barrier to act as a thermal shield to minimize discomfort to human skin in the event of direct contact. In some cases the front frame member 206 includes one or more apertures or windows 212 to facilitate radiation/heat flow and the thermal shielding layer 210 is positioned between the panel 200 and the apertures 212.

According to some embodiments, the thermal shielding layer 210 also acts as a ground plane to shield a sauna user from electric fields generated by the heating panel. In some cases the thermal shielding layer 210 is formed from a conductive fabric and then connected by wire to ground potential through, e.g., the power conductors, the panel frame, a conduit, or another suitable surface or component at ground potential.

Figure 3A:
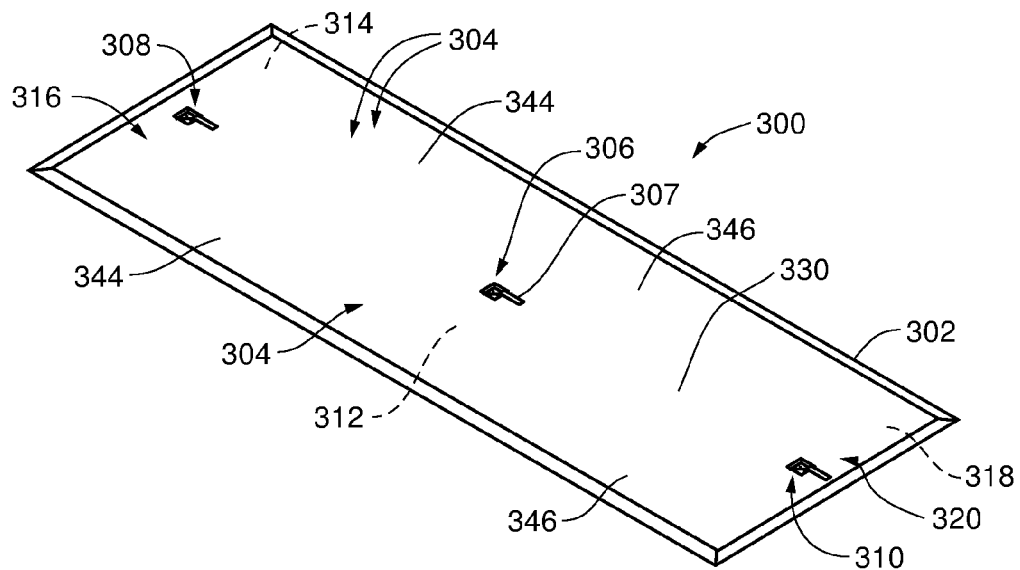
FIG. 3A is a perspective view of an infrared heating panel with three electrical connection points according to an embodiment of the invention.
Figure 3B:
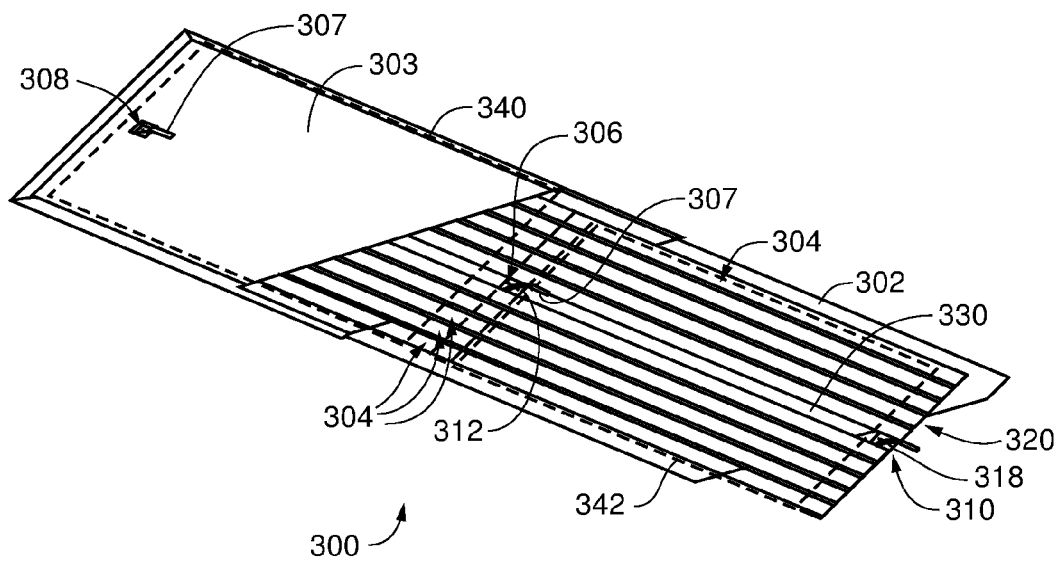
FIG. 3B is a perspective, partial cut-away view of the infrared heating panel of FIG. 3A.

FIGS. 3A-3G are different views of an infrared heating panel 300 with three electrical connection points according to an embodiment of the invention. FIG. 3A is a perspective view of the heating panel 300, while FIG. 3B is a perspective, partial cut-away view of the panel 300 that illustrates the interior construction of the panel 300 according to some embodiments. As shown, the heating panel 300 includes a substrate 302 that supports multiple heating elements 304, which are illustrated with broken lines in FIG. 3A. Three electrical buses 312, 314, 318 extending perpendicularly across the heating elements 304 electrically connect the heating elements together. In this example, the buses also provide three corresponding electrical connection points 306, 308, 310 for connecting a power feed to the heating panel 300 and heating elements 304 within.

In general, the heating panel 300 generates infrared radiation from electrical power applied to the connection points 306, 308, 310, which can then be used to warm a person in close proximity to the panel. In some cases heating panels such as the heating panel 300 may be incorporated in a heating system including multiple heating panels, such as in an infrared sauna (e.g., as shown in FIG. 1). In some cases a heating panel may be useful by itself as a heat generating device. In addition, while several embodiments are described herein in the context of an infrared sauna, it should be appreciated that applications of a heating panel are not so limited and that heating panels in accordance with embodiments of the invention may be useful for many applications in a variety of environments in which a device is desired for producing radiant heat with infrared electromagnetic radiation.

As shown in FIG. 3B, the substrate 302 includes a bottom layer that supports the heating elements 304 and power buses and may also provide a first exterior surface for the panel. The substrate 302 is constructed from an electrically insulative material (e.g., fiberglass) that provides a sturdy base for mounting or attaching the heating elements 304 and/or buses. For example, in some cases the substrate 302 is made from FR-4 sheets of glass reinforced epoxy, such as in a printed circuit board. Of course, the size and dimensions of the substrate 302 and the heating panel 300 itself can vary according to the space requirements needed for a particular design and the invention is not limited to any particular size and/or shape for the substrate. The heating panel 300 also includes a top layer 303 that provides an insulative cover over the heating elements. In some cases the top layer 303 includes an opening adjacent to each of the power buses, which provides access to each of the power buses and defines the electrical connection points 306, 308, 310 for connecting a power feed to the heating panel 300. In this embodiment the heating panel 300 can be connected to a power supply via one or more wires 307 attached (e.g., soldered) to the panel at the connection points with solder wells 360.

The infrared heating panel 300 can be made in any suitable manner, and in some cases is formed as a laminate stack of multiple layers at certain locations in the panel, including for example the substrate 302, the power buses, and the heating elements 304. Other layers may also be present in between or exterior to the illustrated layers. Those skilled in the art will appreciate that many variations in the construction of the infrared heating panel 300 are possible. U.S. patent application Ser. No. 12/966,221, filed Dec. 13, 2010, provides additional details about the construction of infrared heating panels such as the heating panel 300, and is incorporated herein by reference in its entirety.

Figure 3C:
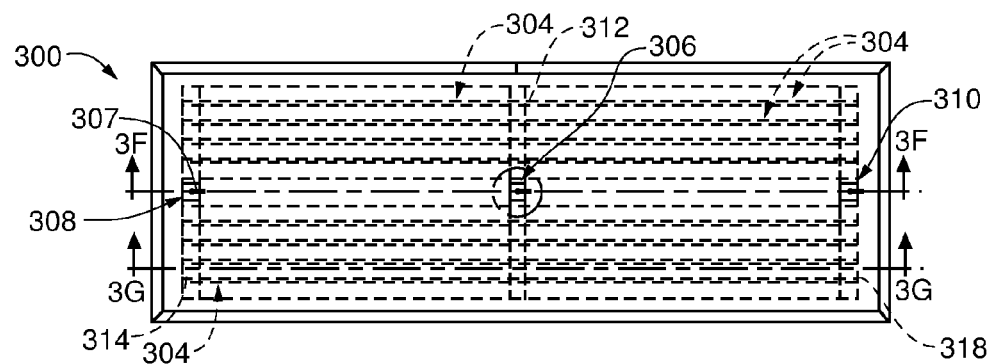
FIG. 3C is a surface view of the infrared heating panel of FIG. 3A.
Figure 3D:
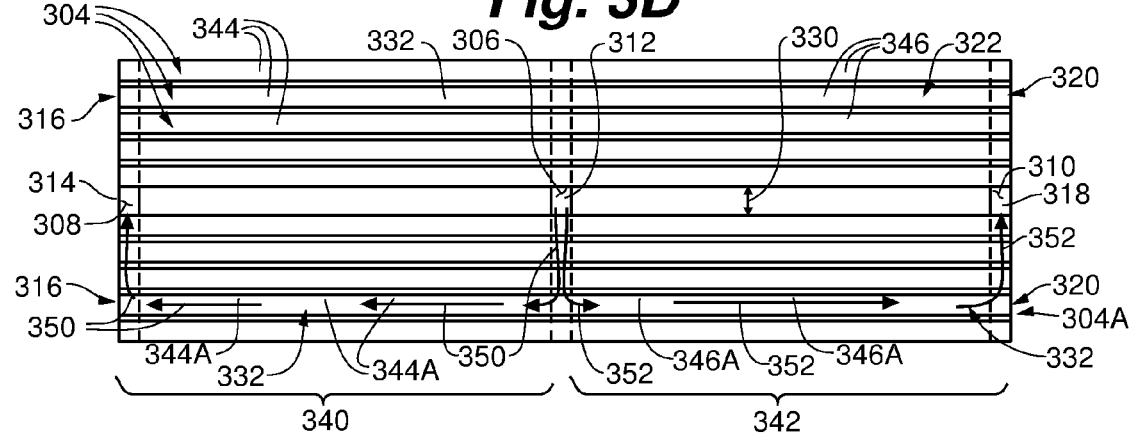
FIG. 3D is a surface view of the configuration of infrared heating elements of the heating panel of FIG. 3C.
Figure 3E:
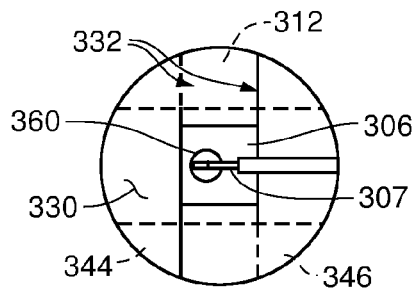
FIG. 3E is an enlarged view of a portion of the heating panel in FIG. 3C.

FIG. 3C is a surface view of the infrared heating panel 300 and shows with broken lines the relative placement of the heating elements 304 within the panel. FIG. 3D provides an enlarged, separate view of the heating elements 304 connected together by the power buses. As shown in the figures, in this embodiment the heating elements 304 are electrically connected together by the first bus 312. The second electrical bus 314 also connects the heating elements together at one end 316 of the heating elements, and the third bus 318 also provides a common electrical connection that is positioned at the opposite panel end 320 of the heating elements. In this embodiment the heating elements 304 are electrically coupled to the connection points 306, 308, 310 with each of the first, second, and third buses respectively. Of course, other methods of powering the heating elements 304 are also possible, including by individual twisted pair power conductors connecting portions of each individual heating element 304 to a power source.

Referring to FIG. 3D, in some cases the heating elements 304 are arranged adjacently in a row configuration, though it is contemplated that in some cases a heating panel may only include a single heating element or many more heating elements than are shown in the figures. As shown in this example, the row of elements is separated into two groups of heating elements 304 separated by a small gap 330 that leaves room for the electrical connection points. Of course this is just one possible arrangement of the heating elements 304 and in some cases other types of spacing of the elements may be used, including the possibility of no gap 330.

According to some embodiments, the heating elements of an infrared heating panel may have one longitudinal segment extending between buses as shown in FIGS. 3A-3G. In some cases the heating elements may be provided with a second, parallel segment (as shown in FIGS. 8A-8F and also taught in U.S. patent application Ser. No. 12/966,221), in order to reduce and/or cancel electromagnetic radiation generated by currents passing through the heating elements. In the example shown in FIGS. 3A-3G, the heating elements 304 each include an elongated segment 332 that extends between the first end 316 of the heating element and the second end 320 of the heating element. The segment 332 is electrically connected to the second bus 314 at the first end 316 and to the third bus 318 and the second end 320.

The segment 332 is further electrically connected to the first bus 312 at a location between the ends of the heating elements. In some embodiments the position of the first bus 312 relative to the ends of the heating elements marks the location of a change in the power density profile of the heating panel 300. For example, the first bus 312 may physically divide the heating panel 300 into two power density zones 340, 342 and provide an electrical discontinuity along the length of each heating element 304 to generate separate power densities in each of the zones 340, 342.

Figure 3F:
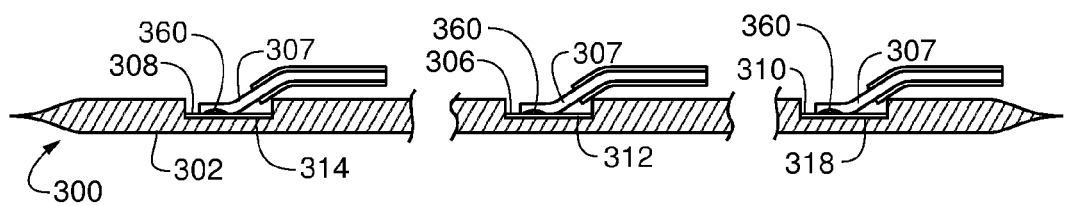
FIG. 3F is a cross-sectional view of the heating panel of FIG. 3C illustrating connection points of the heating panel.
Figure 3G:
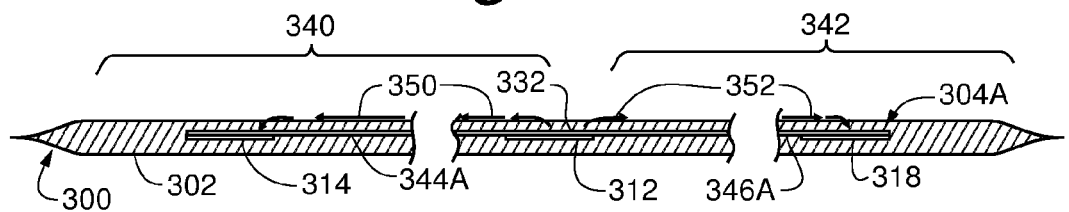
FIG. 3G is a cross-sectional view of the heating panel of FIG. 3C depicting a cross-section of a heating element.

The heating elements 304 of the infrared heating panel 300 are electrically coupled to and receive electrical current from the panel's connection points 306, 308, 310 via the first, second, and third buses. As one example, when a positive voltage (e.g., 120 VAC) is applied to the first electrical connection point 306, and the second connection point 308 is connected to a return conductor or ground conductor (e.g., AC ground) a current will flow between the first and second connection points along a path that includes the first bus 312, a first segment portion 344 of each heating element 304, and the second bus 314. As the current flows through the first segment portion 344 of the heating elements, the segment portion 344 generates corresponding infrared radiation. A representative illustration of the current path for a particular heating element 304A is shown in FIG. 3D by arrows 350 illustrating current flow through the first segment portion 344A. FIG. 3G provides a cross-sectional view of the heating panel 300 at the same heating element 304A, also showing the current path 350 through the first segment portion 344A.

In the case that a second return conductor or ground conductor is connected to the third connection point 310, a similar but distinct current path will develop through the first and third buses and a second portion 346 of each of the heating elements 304. A representative illustration of this current path for one particular heating element 304A is shown in FIG. 3D by arrows 352 illustrating current flow through first segment portion 346A. Of course other wiring schemes are contemplated, including the use of the first segment portion 344, the second segment portion 346 and/or both portions simultaneously.

Accordingly, as power is applied to the heating panel 300, two separate currents will flow through each heating element segment 332, giving rise to two separate amounts of power and power densities for each heating element 304. The combination of the power buses in connection with the heating elements thus provide a power density profile along the length of a single heating element 304. The profile includes at least a first power density associated with the first segment portion 344, a second power density associated with the second segment portion 346, and a transition point or discontinuity in the profile associated with the first power bus 312 between the first and second segment portions 344, 346. The combination of first power densities generated by the first segment portion 344 of all of the adjacent heating elements 304 thus creates the first separate zone 340 of power density. Likewise, the combination of second power densities generated by the second segment portion 344 of all of the adjacent heating elements 304 thus creates the second separate power density zone 342 of on the panel.

Figure 4A:
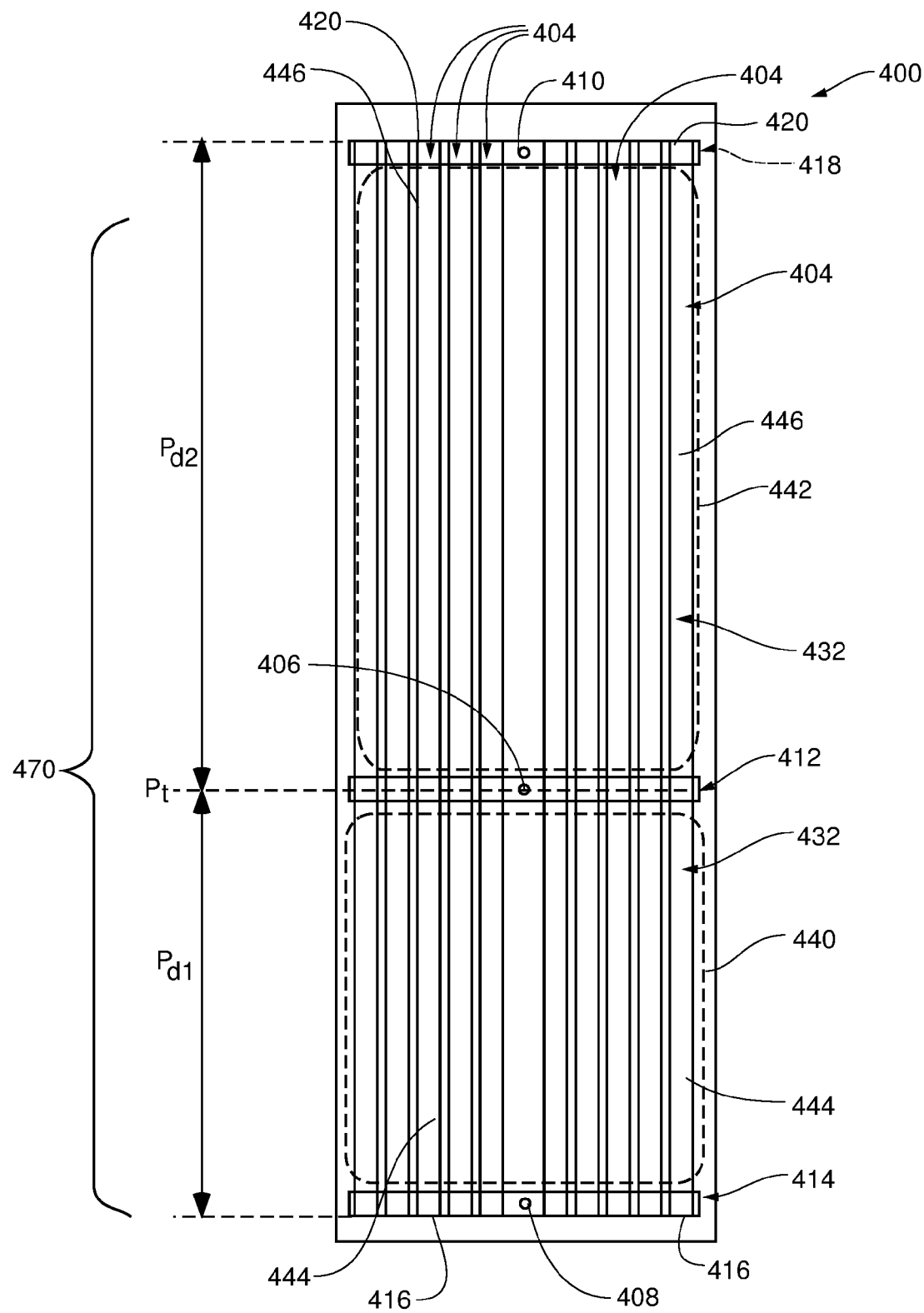
Figure 5A:
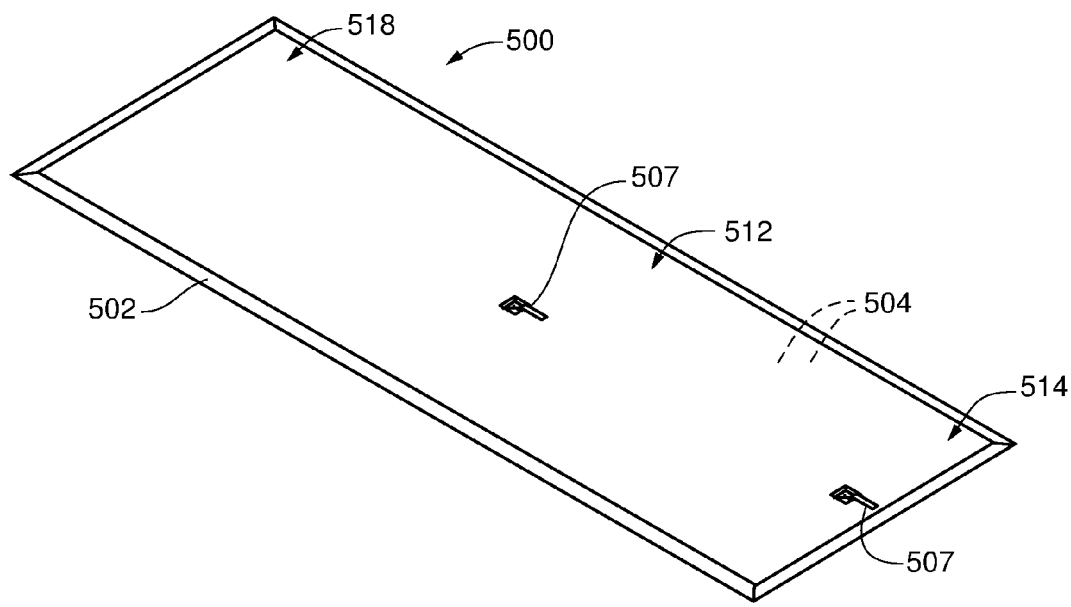
FIG. 5A is a perspective view of an infrared heating panel with two electrical connection points according to an embodiment of the invention.
Figure 5B:
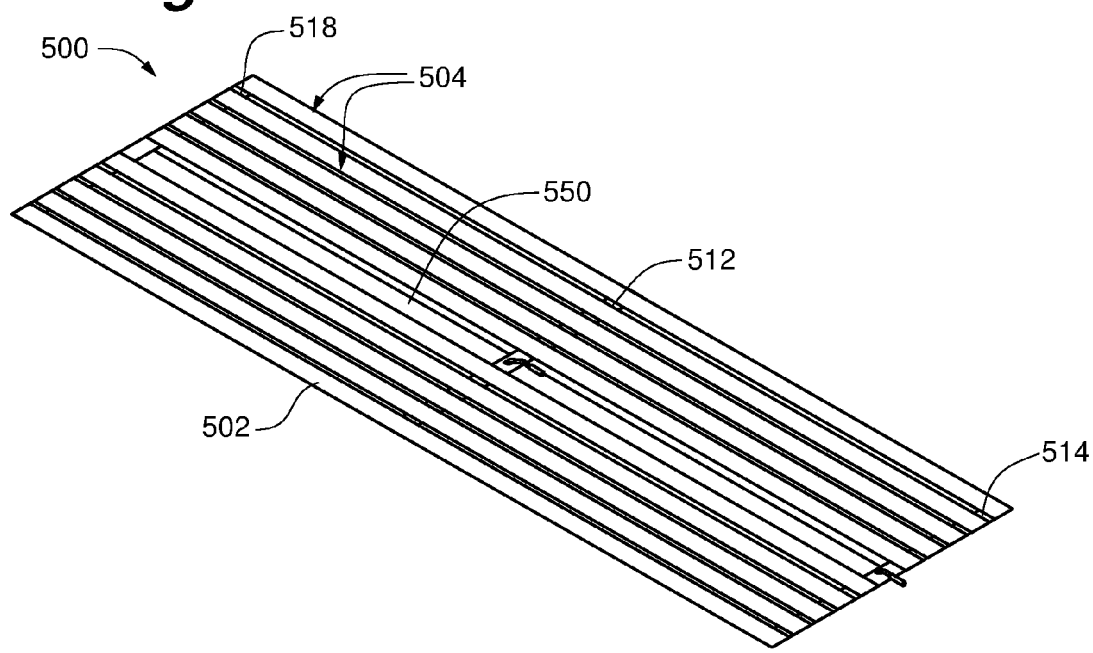
FIG. 5B is a perspective view of a configuration of infrared heating elements of the heating panel of FIG. 5A.
Figure 5C:
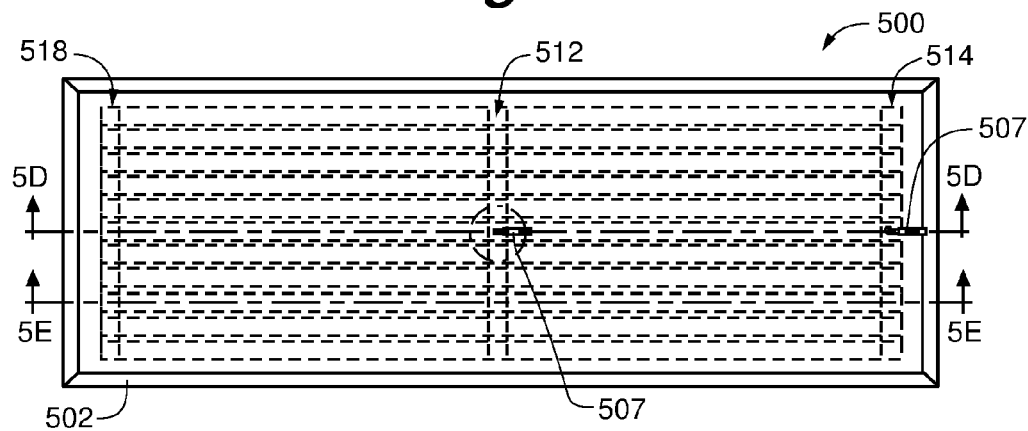
FIG. 5C is a surface view of the infrared heating panel of FIG. 5A.
Figure 5D:
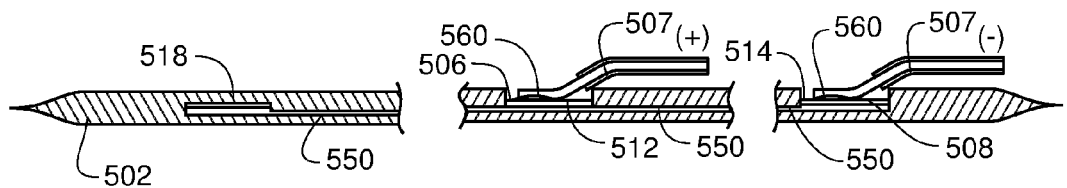
FIG. 5D is a cross-sectional view of the heating panel of FIG. 5C illustrating connection points of the heating panel.
Figure 5E:
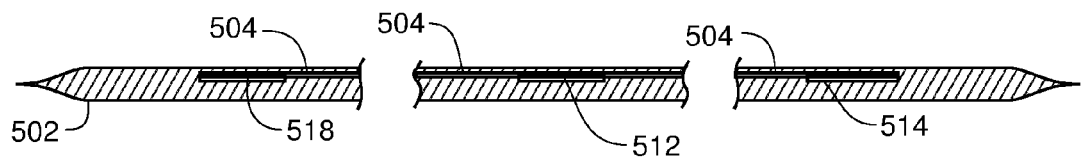
FIG. 5E is a cross-sectional view of the heating panel of FIG. 5C depicting a cross-section of a heating element.

FIG. 4A is a surface view of an infrared heating panel 400 depicting a configuration of heating elements 404 according to some embodiments of the invention. As previously discussed, in some cases the size and shape of each separate zone 440, 442 of power density can be set by positioning the first bus 412 at a particular location between the ends of the heating elements 404. Further, in some cases positioning the first bus 412 at a particular location can also determine, at least in part, the amount of power that will be generated by each segment portion 444, 446 of each heating element 404. Thus, while the first bus 412 may be positioned to create separate zones on the heating panel with the same or very similar power densities, the first bus may also be positioned such that each separate zone on the heating panel generates a different power density, and in turn a different amount of infrared radiation and corresponding heat for a sauna user.

As taught in U.S. patent application Ser. No. 12/966,221, in some embodiments the first segments 432 of the heating elements 404 can be formed from strips of an electrically resistive (e.g., semi-conducting) thin film material adapted to emit infrared radiation in response to a current flowing through the material. In some cases the material is a carbon-based thin film. The choice of resistive material and dimensions of the resistive material strip forming the first segments 432 can vary depending upon the desired power and heat generation and the performance characteristics (e.g., resistivity) of the material. In one embodiment each of the first segments 432 are formed from a carbon-based resistive material having a resistivity of about 20 ohms per square centimeter at a thickness of 0.4 millimeters.

A resistive thin film may be formed upon the substrate in any suitable manner, including by thin film deposition or etching. Another method of forming the thin film includes screen printing using a carbon based ink, such as a colloidal graphite ink. One example of a carbon-based material provided in U.S. patent application Ser. No. 12/966,221, and also described in U.S. patent application Ser. No. 12/573,882, the entire content of which is hereby incorporated by reference. U.S. Pat. No. 4,485,297 illustrates additional examples of resistive/semi-conductive materials, and its entire content is hereby incorporated by reference as well.

Returning to FIG. 4A, the infrared heating panel includes a configuration of heating elements 404 arranged in an adjacent, parallel manner similar to the embodiment shown in FIGS. 3A-3G. Each of the heating elements 404 in this case are electrically connected by the first electrical bus 412. The second electrical bus 414 is positioned across the heating elements 404 to mechanically and electrically connect the elements at a first end 416 of the elements. As depicted in FIG. 4A, the heating panel 400 has a vertical orientation similar to the panels 110A, 110B in FIG. 1. Thus, the first end 416 of the heating elements is also their bottom end 416. Similarly, the third electrical bus 418 mechanically and electrically connects the heating elements at their second end 420, which is also the top end 420 of the heating elements in the vertical orientation.

As depicted in FIG. 4A, the first bus 412 crosses the heating element segments 432 at a location that is between the top and bottom ends 420, 416 of the heating elements 404. Thus, the first bus 412 effectively divides each heating element segment 432 into a first segment portion 444 and a second segment portion 446 as described earlier. The combination of the multiple first segment portions 444 of the heating elements thus forms a first power density zone 440 near the bottom end 416 of the heating elements. Similarly, the combination of the multiple second segment portions 446 of the heating elements forms the second power density zone 442 nearer the top end 420 of the heating elements.

According to some embodiments, the position of the first bus 412 relative to the ends of the heating elements 404 can be set so that each of the first and second power density zones generates a different power density during operation of the panel 400. For example, in some cases each of the heating element segments 432 are formed from a resistive material that has a uniform resistivity along the entire length of the segment 432. With the first bus 412 located closer to the bottom end 416 of the segments, the total resistance encountered by a current flowing through the first segment portions 444 will be less than the total resistance encountered by a current flowing through the second segment portions 446. Forming the first power density zone 440 with a lower total resistance generates more total power and thus a greater power density than the second power density zone 442, which exhibits a higher total resistance, and thus less total power, over a greater surface area.

It should be appreciated that some embodiments of the invention enable the creation of separate power density zones and corresponding separate heat zones on a heating panel with heating elements that are each formed from one strip of resistive material. Accordingly, separate and/or multiple resistive strips are not needed for each heating element in this case. Instead, a heating panel in these embodiments can electrically divide each single resistive strip 432 into at least two functionally separate segment portions 444, 446. Thus it should be appreciated that the heating panel's design and manufacture can be simplified (e.g., one resistive strip per heating element instead of two or more) while also providing additional functionality from two separate power density zones 440, 442 and heat zones.

The position of the first power bus 412 thus creates a changing power density profile 470 for the heating panel 400 with respect to its length from the top of the panel to the bottom of the panel. In this example, the power density profile 470 includes a relatively constant first power density $P_{d1}$ corresponding to the first zone 440, a transition point $P_t$ corresponding to the first bus 412, and a relatively constant second power density $P_{d2}$ corresponding to the second zone 442. Of course a heating panel as taught herein can be formed with any one of a wide variety and number of different power density profiles (and associated heat profiles). In addition, while the examples described herein portray two adjacent zones of different power density, embodiments are not limited to only two separate zones. Instead it is contemplated that two, three, or more separate zones of power density and heat may be provided.

FIGS. 4A, 4B, and 4C each illustrate an example of a different heating element configuration generating a correspondingly different power density profile. In the example of FIG. 4A, the first bus 412 is positioned relative to the top and bottom ends of the heating elements such that the ratio of the power density of the first zone 440 to that of the second zone 442 is approximately 1.5. In this embodiment with heating segments 432 having uniform dimensions and resistivity along their entire length, the first bus's location is set such that the ratio of the length of the first segment portion 444 to the length of the second segment portion 446 is approximately 2 to 3.

It will be appreciated that the absolute value of the power generated by the first and second zones 440, 442 will depend upon the applied current and/or voltage from the power supply, as well as the size, shape, and physical properties (e.g., resistivity) of the heating element segments 432. While many power density profiles are possible, in one embodiment the heating panel 400 is configured to generate up to 150 W, with the first zone generating about 90 W and the second zone generating about 60 W. In this case the panel is approximately 90 cm long by about 30 cm wide, each heating element segment is about 2 cm wide, and the first bus is located approximately 34 cm from the bottom end of the heating elements and approximately 51 cm from the top end of the heating elements.

FIGS. 4B and 4C illustrate examples of infrared heating panels 480, 490 respectively, in which different zones of the panels have different power densities, but also wherein the power ratio of a first zone to a second zone of the panel is somewhat less than the ratio of 1.5 of the example in FIG. 4A. For example, the panel 480 includes a first power density zone 440 and a second power density zone 442 that exhibit a ratio of power generation of about 1.3. In some cases that ratio corresponds to the first zone 440 generating about 87 W and the second zone 442 generating about 68 W. The panel 490 of FIG. 4C includes a first power density zone 440 and a second power density zone 442 that exhibit a ratio of power generation of about 1.1. One example of actual powers that can be generated with a 1.1 ratio is 80 W generated by the smaller first power density zone 440 and 70 W generated by the larger power density zone 442.

Of course other ratios of power generation and amounts of total power may also be provided. According to some embodiments, the power ratio may be increased by decreasing the length of the first segment portion 444 and/or increasing the length of the second segment portion 446. According to some embodiments, the ratio of the power generated by the first power density zone 440 to power of the second power density zone 442 may be 1, corresponding to separate power density zones of similar or the same size (i.e., the first bus 412 is attached to the heating element segments 432 at approximately the midpoint between the top and bottom ends of the segments 432. According to some embodiments it is contemplated that the ratio of power densities of the first power zone 440 to the second power zone 442 may be greater than 1.5. For example, the lengths of the first segment portions 444 may be shortened further relative to the lengths of the second segment portions 446. According to some embodiments, the power density of each of the separate power density zones 440, 442 is based upon and/or limited by the properties of the substrate material and/or the heating element material. For example, in some cases the ratio of power densities may only be as great as a value corresponding to a maximum current, maximum voltage, and/or maximum power rating for the substrate and heating element material.

Although not depicted, it is also contemplated that in some cases it may be useful to change the relative power density by establishing further differences between the first and the second segment portions 444, 446. For example, while in many cases the first and the second segment portions 444, 446 have the same width and the same uniform resistivity throughout (due to their common forming as part of the heating element segment 432) it is contemplated that changes to the width and/or resistivity of one or both of the first and second segment portions may be made if desired.

Referring again to FIG. 1 in combination with FIGS. 4A-4C, Applicant has discovered that configuring an infrared heating panel with at least two separate zones of power density and temperature can help mitigate and/or eliminate the 'chimney effect' seen in older styles of infrared heating panels. For example, in certain embodiments reduction of such an effect is observed when mounting a heating panel such as one of panels 400, 480, and 490 in a vertical orientation within a sauna as in FIG. 1. Mounting the panel in a vertical orientation locates the first power density zone 440 at the bottom of the panel nearer the floor of the sauna. A vertical orientation also positions the second power density zone 442 near the top edge of the infrared heating panel nearer the ceiling of the sauna. According to some embodiments, the 'chimney effect' of heat escaping from the lower parts of the heating panel and rising toward the top of the panel can be counteracted by increasing the power density, and thus temperature, of the first, lower positioned zone 440, while reducing the power density and temperature of the higher positioned zone 442.

The embodiments described above with respect to FIGS. 3A-3G and 4A-4C illustrate examples of non-linear infrared heating panels that include three electrical connection points for applying power to the panels. As shown, each heating panel includes a first electrical connection point 306, 406 located on the first power bus, centered with the width of the panel in these examples. Second and third electrical connection points 308/310, 408/410 are located on the second and third power buses, respectively, to enable a voltage from a power source to be applied across each of the first segment portions 344, 444 and the second segment portions 346, 446. In some cases power is applied to one or more of the electrical connections through the wires of a power feed that are attached to the connection points, as in the example of the wires 307 being fastened to the connection points as shown in FIG. 3F with a solder well 360.

FIGS. 5A-5E and 6A-6G illustrate two additional examples of electrical connection configurations according to some embodiments. Turning to FIGS. 5A-5E, in this example, the heating panel 500 is similar in many respects to the examples described above, and includes a substrate 502 supporting a configuration of heating elements 504 electrically connected together by a first bus 512, a second bus 514, and a third bus 518. The heating panel 500 further includes a return segment 550 that extends between and electrically connects the second and third power buses 514, 518. As shown, use of an integral return segment 550 can allow for more convenient connection of the heating panel 500 to a power source using only two feed wires 507 fastened at the electrical connection points 506, 508 with a solder well 560.

Figure 6A:
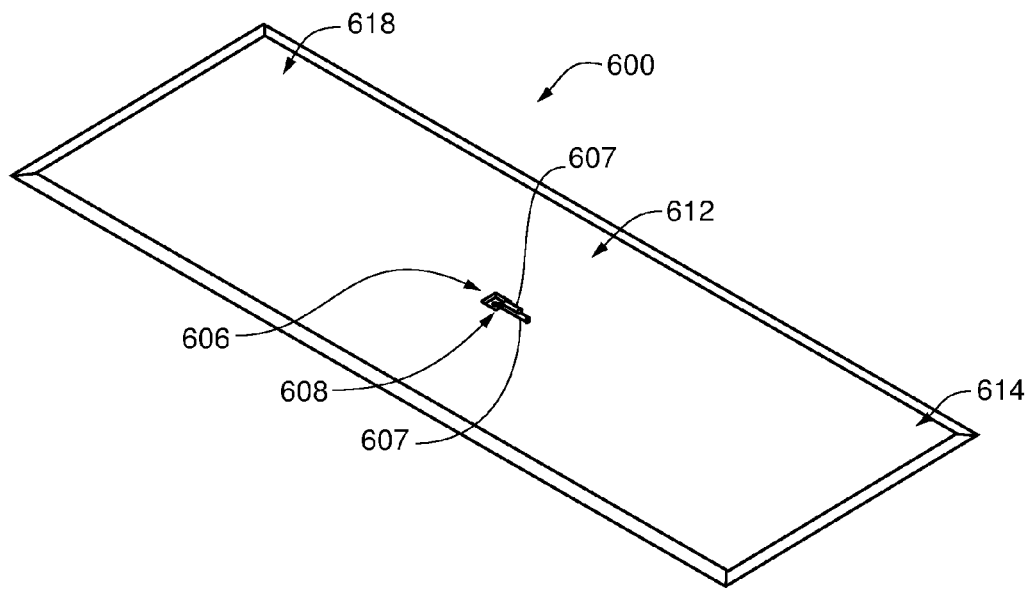
FIG. 6A is a perspective view of an infrared heating panel with one electrical connection location according to an embodiment of the invention.
Figure 6B:
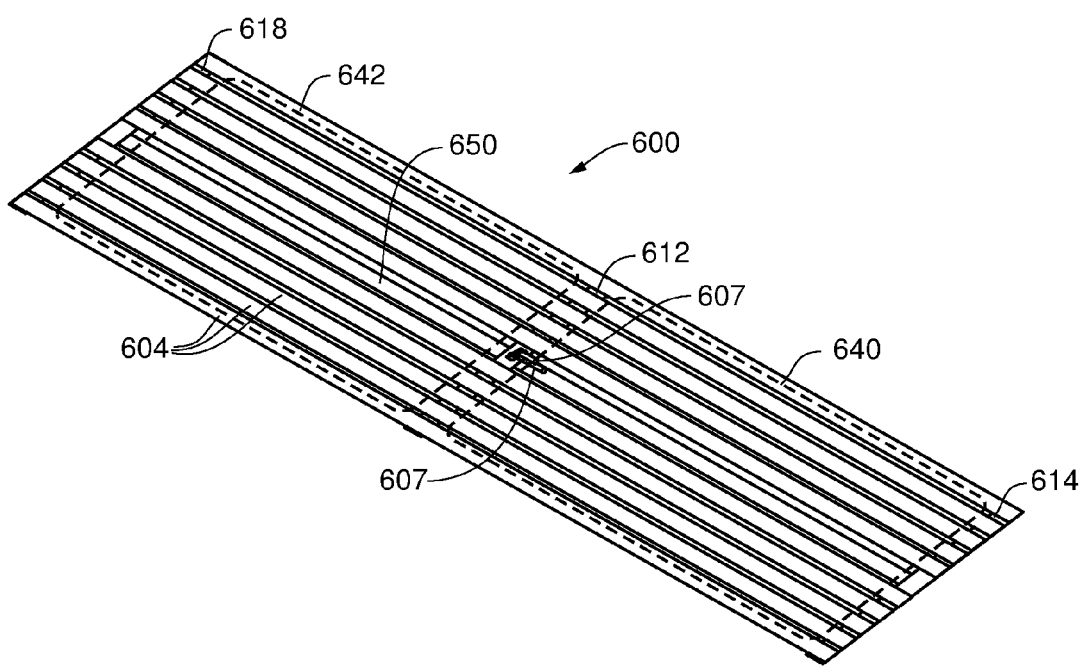
FIG. 6B is a perspective view of a configuration of infrared heating elements of the heating panel of FIG. 6A.
Figure 6C:
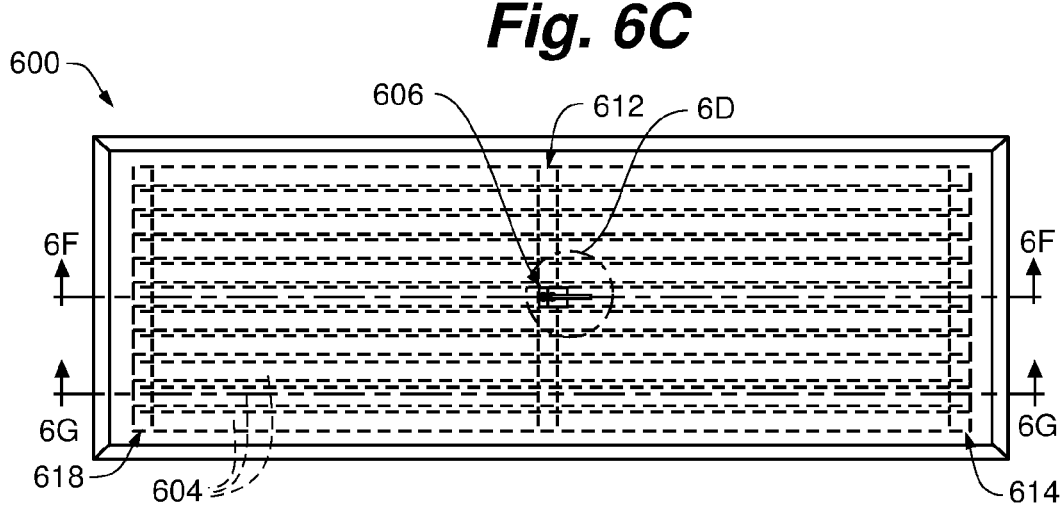
FIG. 6C is a surface view of the infrared heating panel of FIG. 6A.
Figure 6D:
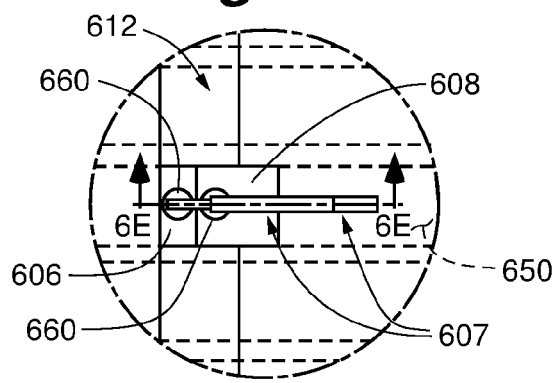
FIG. 6D is an enlarged view of a portion of the heating panel in FIG. 6C.
Figure 6E:
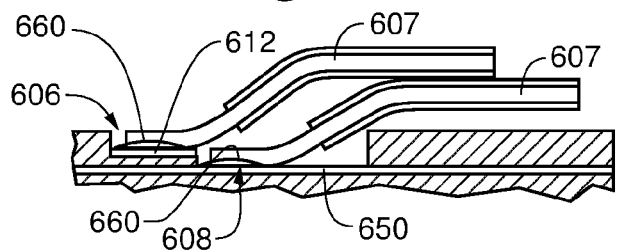
FIG. 6E is a cross-sectional view of the portion of the heating panel shown in FIG. 6D.
Figure 6F:
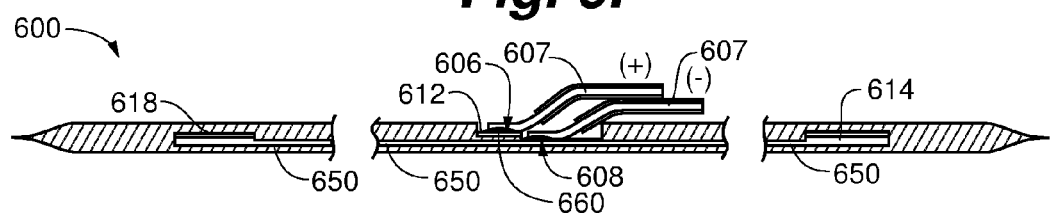
FIG. 6F is a cross-sectional view of the heating panel of FIG. 6C illustrating a common connection location of the heating panel.
Figure 6G:
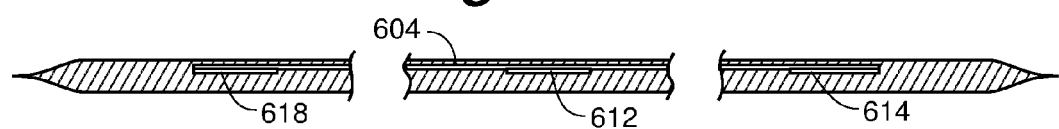
FIG. 6G is a cross-sectional view of the heating panel of FIG. 6C depicting a cross-section of a heating element.

Turning to FIGS. 6A-6G, another example of an alternative connection method is illustrated according to some embodiments. In this example, the infrared heating panel 600 includes three power buses 612, 614, 618 connecting together a plurality of heating elements 604 as in the examples discussed above. A first electrical connection point 606 is provided by the first power bus 612 as shown in FIG. 6D. As shown in FIGS. 6D, 6E, and 6F, in this embodiment a return segment 650 electrically connects together the second bus 614 and the third bus 618 attached to the heating elements 604 at opposite ends of the panel. The return segment 650 includes a second electrical connection point 608 proximate to the first electrical connection point 606. As will be appreciated, this embodiment provides the separate power density zones 640, 642 as in previous embodiments, but also provides a convenient single connection point or location at the pads 606, 608 for connecting two power feed wires 607 (e.g., with a solder well 660) that may run within a single cable jacket, for example.

Electrical connections can be made to an infrared heating panel in a variety of manners, as will be appreciated by those skilled in the art. In the examples described herein, power is applied to various heating panels through single feed wires (illustrated in the drawings as wire stubs) that are connected at their opposite ends to a power source and/or power distribution junction. According to some embodiments, mechanisms for solidifying and strengthening the electrical connections can be employed as shown in FIGS. 7A-7D.

Figure 7A:
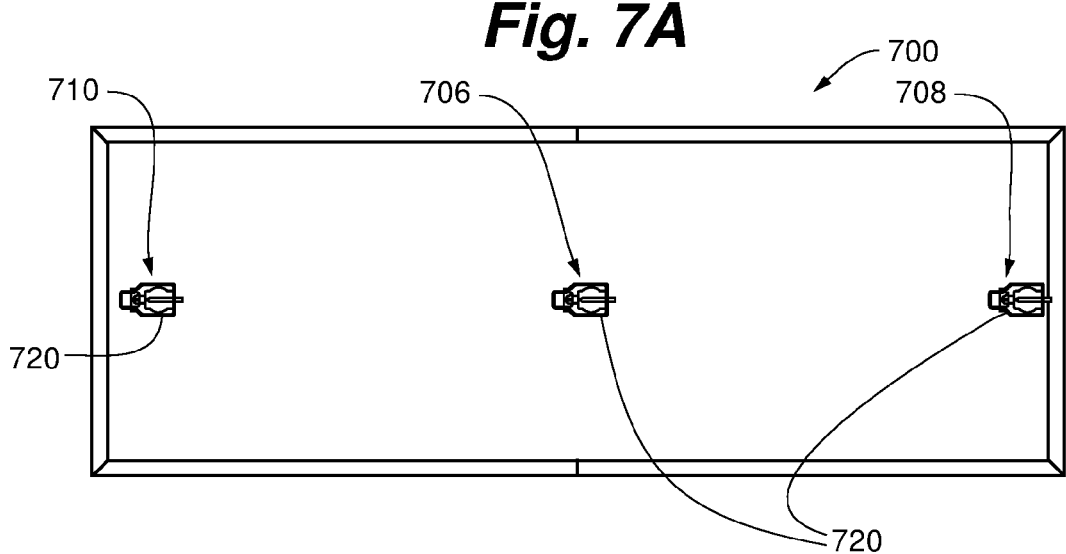
FIG. 7A is a surface view of an infrared heating panel with multiple power feed containment shells according to an embodiment of the invention.
Figure 7B:
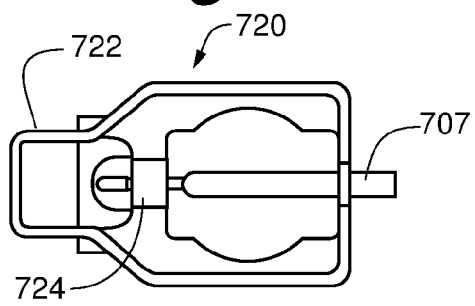
FIGS. 7B-7D are views of various containment shells for a heating panel power feed according to embodiments of the invention.
Figure 7C:
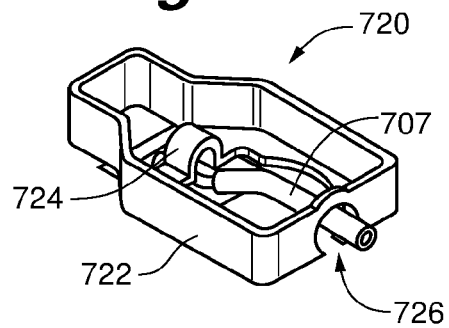
Figure 7D:
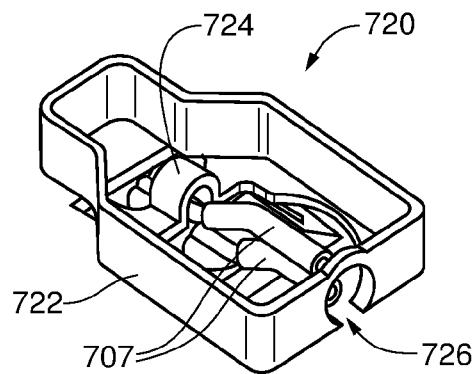

FIG. 7A illustrates a surface view of one infrared heating panel 700 with three electrical connections 706, 708, 710. In this embodiment, the mechanical connection between the heating panel 700 and the wires 707 is strengthened by an epoxy containment shell 720 at each connection location. In this example, the shell 720 includes an outer wall 722 with a reinforcement piece 724 covering the bare wire ends that are soldered to the panel 700 connections. The shell also includes an opening 726 in the wall, allowing the wire (and/or cable, whichever the case may be) to exit the containment shell 720.

After placing the shell about the wire connections, the shell 720 can be filled with an epoxy resin or other insulative fill material to isolate the electrical connection from the surrounding environment and also provide a strong, reinforced bond about the wire to the surface of the heating panel 700. According to some embodiments, use of a wire containment shell 720 as shown in FIGS. 7A-7D can also facilitate the use of certain wire configurations that promote electromagnetic field cancellation. Examples of types of power distribution connections that can also be used for any of the embodiments described herein are taught in U.S. patent application Ser. No. 13/665,040, filed Oct. 31, 2012, the contents of which are hereby incorporated herein by reference.

Turning to FIGS. 8A-8F and 9A-9C, in some embodiments an infrared heating panel 800 may have heating elements that each have parallel and opposite longitudinal segments adapted to reduce and/or cancel electromagnetic fields emanating from the heating elements. Examples of such heating element configurations are taught in U.S. patent application Ser. No. 12/966,221, filed Dec. 13, 2010, the content of which is hereby incorporated by reference. As shown in FIGS. 8A-8F, in some embodiments a heating panel 800 comprises a planar substrate 802 with first and second opposing surfaces. A set of heating elements 804 each includes a first longitudinal segment 832 attached to one surface of the substrate and a second longitudinal segment 834, opposite and parallel with the first longitudinal segment 832. In this embodiment the heating panel 800 can be connected to a power supply via wires 807 attached (e.g., soldered) to the panel at the connection points with solder wells 860.

Figure 8A:
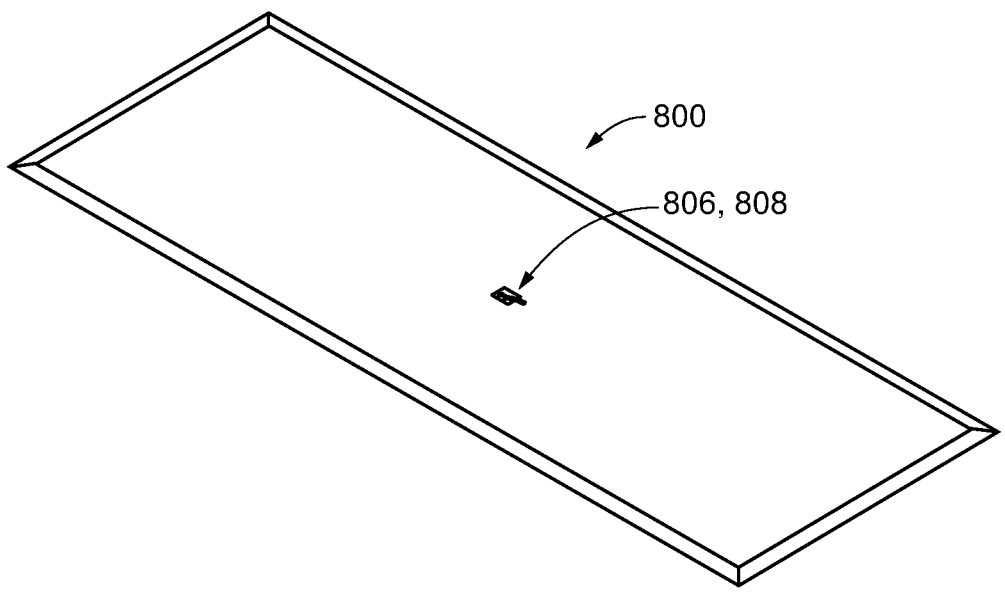
FIG. 8A is a perspective view of an infrared heating panel with one electrical connection location according to an embodiment of the invention.
Figure 8B:
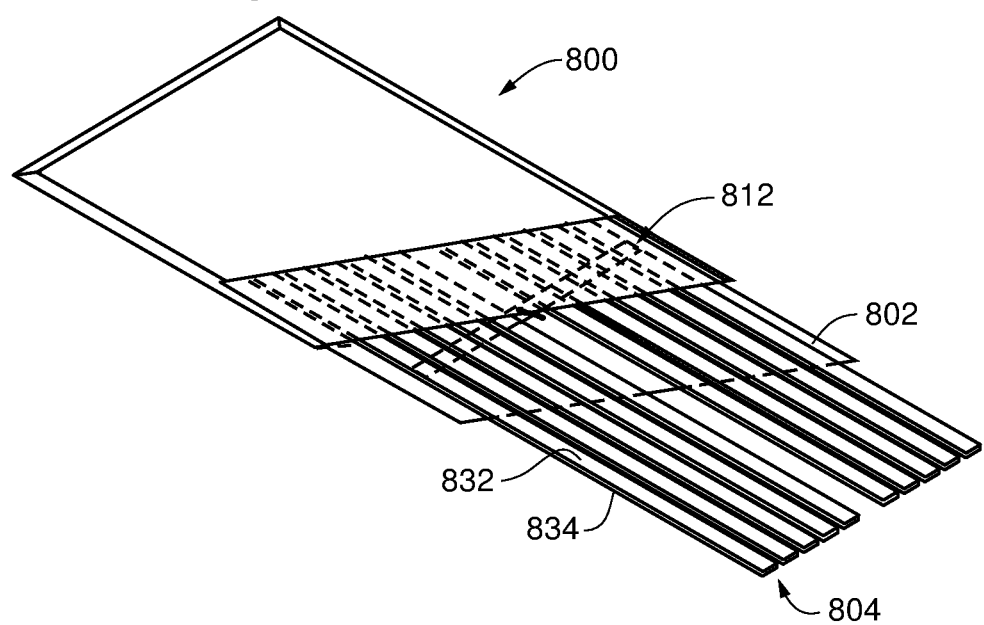
FIG. 8B is a perspective, partial cut-away view of the infrared heating panel of FIG. 8A.

Referring to FIG. 8D, according to one embodiment, a first segment 832 and a second segment 834 are electrically connected together at each end of the segments 832, 834. In this embodiment, the first and second segments 832, 834 are connected together at their segment ends in a location similar to the position of the second and third power buses in earlier embodiments. However, in this case, no power buses connect all of the heating elements together at their ends. Instead, a first power bus 812 is electrically coupled to all of the first segments as shown in FIG. 8B, and the second power bus 814 is electrically coupled to all of the second segments 834, thus enabling a current flowing through the first segment 832 in one direction to be directed back in the opposite direction when flowing through the second segment 834. This current flowing in opposite directions helps reduce and/or cancel electromagnetic fields by generating fields with opposite polarities as taught in U.S. patent application Ser. No. 12/966,221.

Figure 9A:
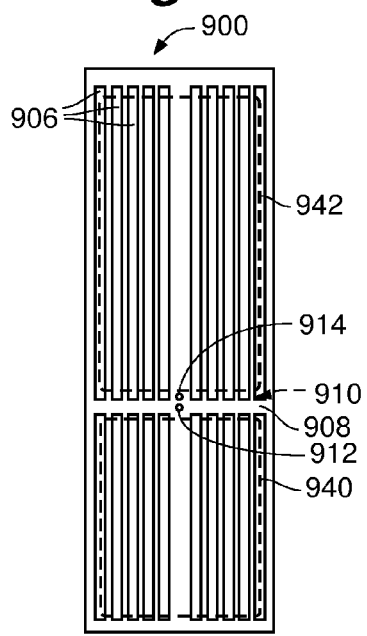
FIGS. 9A-9C are surface views of infrared heating panels depicting configurations of heating elements according to various embodiments of the invention.
Figure 9B:
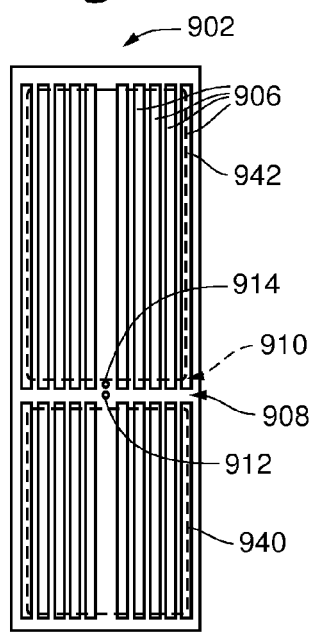
Figure 9C:
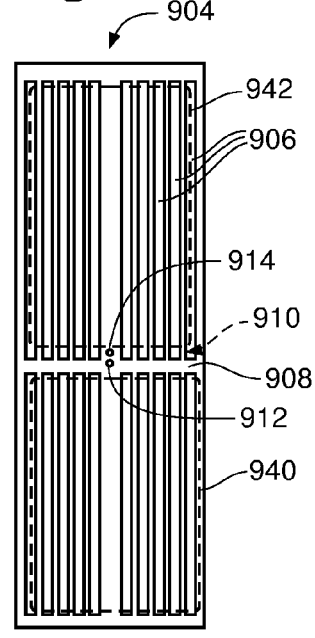

As with earlier embodiments described herein, in certain cases heating panels having a set of heating elements with a cancelling configuration as shown in FIGS. 8A-8F, may also be configured to provide separate power density zones as described above. FIGS. 9A-9C provide surface views of three examples of a heating panel with a field cancelling configuration combined with non-linear power density and heat profiles. As shown, in each case the heating panel 900, 902, 904 includes a plurality of heating elements 906 that are electrically coupled with a first power bus 908 and a second power bus 910. Two electrical connection points 912, 914 are provided in connection with the power buses, enabling a power feed to be connected to the panel. As shown in FIGS. 9A-9C, the position of the first power bus 908 with respect to the ends of the heating panels can be changed in different embodiments in order to provide first and second power density zones 940, 942 having different power densities.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. An infrared heating panel, comprising:
a first power density zone;
a second power density zone;
an electrically insulative planar substrate;
a plurality of infrared heating elements carried by the substrate, each heating element comprising a first end, a second end, and an elongated segment extending between the first end and the second end; and
at least a first power bus and a second power bus, each of the first and the second power buses extending perpendicularly across and electrically connecting with each of the plurality of heating elements;

wherein the first power bus is electrically connected to the elongated segments between the first end and the second end of each of the heating elements; and wherein the elongated segment of each heating element comprises
- an electrically resistive material adapted to emit infrared radiation in response to a current flow,
- a first segment portion extending into the first power density zone between the first power bus and the first end of the heating element, the first segment portion configured to generate a first power density in response to a current flow, and
- a second segment portion extending into the second power density zone between the first power bus and the second end of the heating element, the second segment portion configured to generate a second power density in response to a current flow, the second power density being separate from the first power density.

2. The infrared heating panel of claim 1, wherein the first power density zone is between the first power bus and the first ends of the elongated segments, and wherein the second power density zone is between the first power bus and the second ends of the elongated segments.

3. The infrared heating panel of claim 2, further comprising a bottom end proximate the first ends of the elongated segments and a top end proximate the second ends of the elongated segments, wherein the first power density of the first segment portions extending into the first power density zone is greater than the second power density of the second segment portions extending into the second power density zone.

4. The infrared heating panel of claim 3, wherein the first power density is between 1 and about 1.5 times greater than the second power density.

5. The infrared heating panel of claim 1, wherein the first power density is substantially uniform along the first segment portion and the second power density is substantially uniform along the second segment portion.

6. The infrared heating panel of claim 1, wherein the planar substrate comprises a first surface and an opposing second surface;

wherein the elongated segment is a first elongated segment attached to the first surface of the substrate;

wherein each heating element further comprises a second elongated segment electrically connected to the first elongated segment and attached to the second surface opposite from and in a parallel arrangement with the first elongated segment; and wherein the second power bus is opposite the substrate from and in a parallel arrangement with the first power bus, and electrically connected to each of the elongated second segments between the first end and the second end of each of the heating elements such that the first and the second elongated segments of each heating element combine to form two current paths between the first and the second power buses.

7. The infrared heating panel of claim 1, further comprising a third power bus extending perpendicularly across and electrically connecting with each of the plurality of heating elements at the second ends of the heating elements, wherein the second power bus extends perpendicularly across and electrically connects with each of the plurality of heating elements at the first ends of the heating elements, and wherein the first power bus comprises a first electrical connection point and further comprising a second electrical connection point for connecting the heating panel to a power source.

8. The infrared heating panel of claim 7, further comprising a return segment attached to the substrate, the return segment electrically connecting the second power bus and the third power bus, wherein the second power bus or the third power bus provides the second electrical connection point.

9. The infrared heating panel of claim 7, further comprising a return segment attached to the substrate, the return segment electrically connecting the second power bus and the third power bus, wherein the return segment provides the second electrical connection point proximate to the first electrical connection point.

10. An infrared sauna, comprising:

an enclosed room comprising a floor, a ceiling, and a plurality of walls extending between the floor and the ceiling; and at least a first infrared heating panel having a top edge and a bottom edge, the first heating panel mounted to one of the walls in a vertical orientation with the bottom edge nearest the floor and the top edge nearest the ceiling, the first heating panel comprising:
- an electrically insulative planar substrate;
- a plurality of infrared heating elements carried by the substrate, each heating element comprising a bottom end proximate the bottom edge of the heating panel, a top end proximate the top edge of the heating panel, and an elongated segment extending between the bottom end and the top end; and
- at least a first power bus and a second power bus, each of the first and the second power buses extending perpendicularly across and electrically connecting with each of the plurality of heating elements;
- wherein the first power bus is electrically connected to the elongated segments between the bottom end and the top end of each of the heating elements, thereby defining a first power density zone located between the first power bus and the bottom ends of the heating elements and a second power density zone located above the first power density zone between the first power bus and the top ends of the heating elements;
- wherein the first power density zone generates a first power density in response to currents flowing through the heating elements between the first power bus and the bottom ends of the heating elements; and
- wherein the second power density zone generates a second power density in response to currents flowing through the heating elements between the first power bus and the top ends of the heating elements.

11. The infrared sauna of claim 10, wherein the first power density is greater than the second power density.

12. The infrared sauna of claim 10, wherein the elongated segment of each heating element comprises
- an electrically resistive material adapted to emit infrared radiation in response to a current flow,
- a first segment portion extending between the first power bus and the bottom end of the heating element, the first segment portion configured to generate a first segment power density in response to a current flow corresponding to the first power density, and
- a second segment portion extending into the second power density zone between the first power bus and the top end of the heating element, the second segment portion configured to generate a second segment power density in response to a current flow, the first segment power density being separate from the second segment power density.

13. The infrared sauna of claim 12, wherein the first segment portion has a length different than a length of the second segment portion, the first segment power density is different than the second segment power density.

14. The infrared sauna of claim 13, wherein the first segment power density is greater than the second segment power density.

15. The infrared sauna of claim 12, wherein the first segment power density is substantially uniform along the first segment portion and the second segment power density is substantially uniform along the second segment portion.

16. The infrared sauna of claim 10, wherein the first power density is between 1 and about 1.5 times greater than the second power density.

17. The infrared sauna of claim 10, further comprising a third power bus extending perpendicularly across and electrically connecting with each of the plurality of heating elements at the top ends of the heating elements, wherein the second power bus extends perpendicularly across and electrically connects with each of the plurality of heating elements at the bottom ends of the heating elements, and wherein the first power bus comprises a first electrical connection point and further comprising a second electrical connection point for connecting the heating panel to a power source.

18. The infrared sauna of claim 17, further comprising a return segment attached to the substrate, the return segment electrically connecting the second power bus and the third power bus, wherein the second power bus or the third power bus provides the second electrical connection point.

19. The infrared sauna of claim 17, further comprising a return segment attached to the substrate, the return segment electrically connecting the second power bus and the third power bus, wherein the return segment provides the second electrical connection point proximate to the first electrical connection point.

20. A method for heating an infrared sauna, comprising:
applying power to one or more infrared heating panels, each infrared heating panel having a top edge and a bottom edge, the heating panel mounted to a wall of the sauna in a vertical orientation with the bottom edge nearest a floor of the sauna and the top edge nearest a ceiling of the sauna, each infrared heating panel comprising an electrically insulative planar substrate, a plurality of infrared heating elements, a first power bus, and a second power bus, each heating element comprising an elongated segment extending between a bottom end of the heating element proximate the bottom edge of the heating panel and a top end of the heating element proximate the top edge of the heating panel;
introducing first and second currents from the first power bus into respective first and second portions of the elongated segment of each of the heating elements;
flowing the first current through the first portion of the elongated segment between the first power bus and the bottom end of the heating element to generate infrared radiation at a first power density for heating a human in the infrared sauna;
flowing the second current through the second portion of the elongated segment between the first power bus and the top end of the heating element to generate infrared radiation at a second power density different than the first power density.

* * * * *